(12) United States Patent
Eldridge et al.

(10) Patent No.: US 7,824,420 B2
(45) Date of Patent: *Nov. 2, 2010

(54) IMPLANTABLE PROSTHESIS

(75) Inventors: Stephen N. Eldridge, Exeter, RI (US); Roger Darois, Foster, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 705 days.

This patent is subject to a terminal disclaimer.

(21) Appl. No.: 10/853,823

(22) Filed: May 26, 2004

(65) Prior Publication Data

US 2004/0215219 A1 Oct. 28, 2004

Related U.S. Application Data

(63) Continuation of application No. 10/040,936, filed on Jan. 7, 2002, now Pat. No. 6,790,213.

(51) Int. Cl.
*A61B 17/08* (2006.01)
*A61F 2/02* (2006.01)

(52) U.S. Cl. .................................. 606/151; 623/23.72

(58) Field of Classification Search ................ 606/151, 606/76, 77, 74, 154; 602/42–48; 623/15.12, 623/14.13, 20.17, 23.76, 23.72–23.75; 600/37
See application file for complete search history.

(56) References Cited

U.S. PATENT DOCUMENTS

| | | | |
|---|---|---|---|
| 2,621,145 A | 12/1952 | Sano | |
| 2,671,444 A | 3/1954 | Pease, Jr. | |
| 3,054,406 A | 9/1962 | Usher | |
| 3,124,136 A | 3/1964 | Usher | |
| 3,272,204 A | 9/1966 | Artandi et al. | |

(Continued)

FOREIGN PATENT DOCUMENTS

CA 2114282 A1 7/1994

(Continued)

OTHER PUBLICATIONS

Brown, et al "Comparison of prosthetic materials for abdominal wall reconstruction in the presene of contamination and infection" from Annals of Surgery pp. 705-711.

(Continued)

*Primary Examiner*—Julian W Woo
(74) *Attorney, Agent, or Firm*—Wolf, Greenfield & Sacks, P.C.

(57) ABSTRACT

An implantable prosthesis for an anatomical defect, such as a tissue or muscle defect, that promotes tissue or muscle growth into the prosthesis and subsequently strengthens the area of the defect. At least one pocket and preferably two concentric pockets may be provided to aid with manipulating the prosthesis. Where two pockets are used, a barrier or partition exists between the pockets and the outer pocket allows manipulation of the outer periphery. The incidence of postoperative adhesions between a portion of the prosthesis and tissue, muscle or organs may be minimized with the use of a barrier layer. Reinforcing members may be attached to portions of the prosthesis to aid in positioning and deployment in the area of desired coverage without rendering the prosthesis unduly difficult to implant or uncomfortable for the patient. Typically, two concentric members are employed. Further, the prosthesis is constructed to allow it to be provisionally held in place at desired locations by openings in the pockets that allow access for a stapler or sewing device.

54 Claims, 4 Drawing Sheets

U.S. PATENT DOCUMENTS

| | | |
|---|---|---|
| 3,625,209 A | 12/1971 | Clark |
| 3,874,388 A | 4/1975 | King et al. |
| 3,953,566 A | 4/1976 | Gore |
| 3,965,703 A | 6/1976 | Barnhardt |
| 4,000,348 A | 12/1976 | Harlow |
| 4,007,743 A | 2/1977 | Blake |
| 4,031,569 A | 6/1977 | Jacob |
| 4,051,848 A | 10/1977 | Levine |
| 4,147,824 A | 4/1979 | Dettmann et al. |
| 4,187,390 A | 2/1980 | Gore |
| 4,277,429 A | 7/1981 | Okita |
| 4,344,999 A | 8/1982 | Gohlke |
| 4,347,847 A | 9/1982 | Usher |
| 4,385,093 A | 5/1983 | Hubis |
| 4,400,833 A | 8/1983 | Kurland |
| 4,403,604 A | 9/1983 | Wilkinson et al. |
| 4,452,245 A | 6/1984 | Usher |
| 4,478,665 A | 10/1984 | Hubis |
| 4,482,516 A | 11/1984 | Bowman et al. |
| 4,561,434 A | 12/1985 | Taylor |
| 4,576,608 A | 3/1986 | Homsy |
| 4,585,458 A | 4/1986 | Kurland |
| 4,598,011 A | 7/1986 | Bowman |
| 4,633,873 A | 1/1987 | Dumican et al. |
| 4,655,221 A | 4/1987 | Devereux |
| 4,664,669 A | 5/1987 | Ohyabu et al. |
| 4,693,720 A | 9/1987 | Scharnberg et al. |
| 4,710,192 A | 12/1987 | Liotta et al. |
| 4,713,075 A | 12/1987 | Kurland |
| 4,725,279 A | 2/1988 | Woodroof |
| 4,760,102 A | 7/1988 | Moriyama et al. |
| 4,769,038 A | 9/1988 | Bendavid et al. |
| 4,784,899 A | 11/1988 | Ono et al. |
| 4,796,603 A | 1/1989 | Dahlke et al. |
| 4,816,339 A | 3/1989 | Tu et al. |
| 4,840,626 A | 6/1989 | Linsky et al. |
| 4,854,316 A | 8/1989 | Davis |
| 4,871,365 A | 10/1989 | Dumican |
| 4,882,162 A | 11/1989 | Ikada et al. |
| 4,900,629 A | 2/1990 | Pitolaj |
| 4,902,423 A | 2/1990 | Bacino |
| 4,917,089 A | 4/1990 | Sideris |
| 4,923,464 A | 5/1990 | DiPisa, Jr. |
| 4,942,875 A | 7/1990 | Hlavacek et al. |
| 4,955,907 A | 9/1990 | Ledergerger |
| 4,994,084 A | 2/1991 | Brennan |
| 4,997,440 A | 3/1991 | Dumican |
| 5,002,551 A | 3/1991 | Linsky et al. |
| 5,007,916 A | 4/1991 | Linsky et al. |
| 5,032,445 A | 7/1991 | Scantlebury et al. |
| 5,092,884 A | 3/1992 | Devereux et al. |
| 5,098,779 A | 3/1992 | Kranzler et al. |
| 5,100,422 A | 3/1992 | Berguer et al. |
| 5,104,400 A | 4/1992 | Berguer et al. |
| 5,108,420 A | 4/1992 | Marks |
| 5,110,527 A | 5/1992 | Harada et al. |
| 5,116,357 A | 5/1992 | Eberbach |
| 5,116,360 A | 5/1992 | Punchuk et al. |
| 5,122,155 A | 6/1992 | Eberbach |
| 5,141,515 A | 8/1992 | Eberbach |
| 5,141,522 A | 8/1992 | Landi |
| 5,147,384 A | 9/1992 | LaRocca |
| 5,147,401 A | 9/1992 | Bakker et al. |
| 5,192,301 A | 3/1993 | Kamiya et al. |
| 5,195,542 A | 3/1993 | Gazielly et al. |
| 5,217,494 A | 6/1993 | Coggins et al. |
| 5,217,797 A | 6/1993 | Knox et al. |
| 5,222,987 A | 6/1993 | Jones |
| 5,234,739 A | 8/1993 | Tanaru et al. |
| 5,234,751 A | 8/1993 | Harada et al. |
| 5,254,133 A | 10/1993 | Seid |
| 5,258,000 A | 11/1993 | Gianturco |
| 5,282,851 A | 2/1994 | Jacob-LaBarre |
| 5,290,217 A | 3/1994 | Campos |
| 5,292,328 A | 3/1994 | Hain et al. |
| 5,326,355 A | 7/1994 | Landi |
| 5,333,624 A | 8/1994 | Tovey |
| 5,334,217 A | 8/1994 | Das |
| 5,356,432 A | 10/1994 | Rutkow et al. |
| 5,358,678 A | 10/1994 | Nakamura et al. |
| 5,366,460 A | 11/1994 | Eberbach |
| 5,368,602 A | 11/1994 | de la Torre |
| 5,370,650 A | 12/1994 | Tovey et al. |
| 5,397,331 A | 3/1995 | Himpens et al. |
| 5,411,550 A | 5/1995 | Herweck et al. |
| 5,413,597 A | 5/1995 | Krajicek |
| 5,425,740 A | 6/1995 | Hutchinson, Jr. |
| 5,425,744 A | 6/1995 | Fagan et al. |
| 5,433,996 A | 7/1995 | Kranzler et al. |
| 5,456,720 A | 10/1995 | Schultz et al. |
| 5,461,885 A | 10/1995 | Yokoyama et al. |
| 5,480,436 A | 1/1996 | Bakker et al. |
| 5,504,170 A | 4/1996 | Wu |
| 5,505,887 A | 4/1996 | Zdrahala et al. |
| 5,507,811 A | 4/1996 | Koike et al. |
| 5,508,036 A | 4/1996 | Bakker et al. |
| 5,512,624 A | 4/1996 | Howard, Jr. et al. |
| 5,514,231 A | 5/1996 | Thomas |
| 5,514,633 A | 5/1996 | Noguchi et al. |
| 5,519,004 A | 5/1996 | Urry |
| 5,522,896 A | 6/1996 | Prescott |
| 5,545,178 A | 8/1996 | Kensey et al. |
| 5,552,100 A | 9/1996 | Shannon et al. |
| 5,569,273 A | 10/1996 | Titone et al. |
| 5,591,234 A | 1/1997 | Kirsch |
| 5,593,441 A | 1/1997 | Lichtenstein et al. |
| 5,599,606 A | 2/1997 | Disselbeck et al. |
| 5,601,579 A | 2/1997 | Semertzides |
| 5,614,284 A | 3/1997 | Kranzler et al. |
| 5,634,931 A | 6/1997 | Kugel |
| 5,634,944 A | 6/1997 | Magram |
| 5,641,443 A | 6/1997 | Calcote et al. |
| 5,641,571 A | 6/1997 | Mayer et al. |
| 5,645,915 A | 7/1997 | Kranzler et al. |
| 5,653,760 A | 8/1997 | Saffran |
| 5,677,031 A | 10/1997 | Allan et al. |
| 5,677,047 A | 10/1997 | Thomas |
| 5,686,033 A | 11/1997 | Shimizu |
| 5,686,090 A | 11/1997 | Schilder et al. |
| 5,688,836 A | 11/1997 | Yamamoto et al. |
| 5,690,878 A | 11/1997 | Tuminello et al. |
| 5,695,525 A | 12/1997 | Mulhauser et al. |
| 5,697,390 A | 12/1997 | Garrison et al. |
| 5,697,978 A | 12/1997 | Sgro |
| 5,698,300 A | 12/1997 | Wimmer et al. |
| 5,708,044 A | 1/1998 | Branca |
| 5,713,842 A | 2/1998 | Kay |
| 5,716,408 A | 2/1998 | Eldridge et al. |
| 5,716,409 A | 2/1998 | Debbas |
| 5,721,023 A | 2/1998 | Ostapchenko |
| 5,722,992 A | 3/1998 | Goldmann |
| 5,725,577 A | 3/1998 | Saxon |
| 5,733,337 A | 3/1998 | Carr, Jr. et al. |
| 5,741,297 A | 4/1998 | Simon |
| 5,743,917 A | 4/1998 | Saxon |
| 5,759,204 A | 6/1998 | Seare, Jr. |
| 5,766,246 A | 6/1998 | Mulhauser et al. |
| 5,769,864 A | 6/1998 | Kugel |
| 5,788,626 A | 8/1998 | Thompson |
| 5,795,584 A | 8/1998 | Totakura et al. |
| 5,813,975 A | 9/1998 | Valenti |
| 5,824,082 A | 10/1998 | Brown |
| 5,836,961 A | 11/1998 | Kieturakis et al. |
| 5,855,613 A | 1/1999 | Antanavich et al. |

| | | |
|---|---|---|
| 5,861,034 A | 1/1999 | Taira et al. |
| 5,871,498 A | 2/1999 | Jervis et al. |
| 5,879,366 A | 3/1999 | Shaw et al. |
| 5,916,225 A | 6/1999 | Kugel |
| 5,919,232 A | 7/1999 | Chaffringeon et al. |
| 5,922,026 A | 7/1999 | Chin |
| 5,954,767 A | 9/1999 | Pajotin et al. |
| 5,965,074 A | 10/1999 | Aubertin et al. |
| 5,972,007 A | 10/1999 | Sheffield et al. |
| 5,972,008 A | 10/1999 | Kalinski et al. |
| D416,327 S | 11/1999 | Kugel |
| 5,990,378 A | 11/1999 | Ellis |
| 5,990,380 A | 11/1999 | Marotta et al. |
| 6,004,333 A | 12/1999 | Sheffield et al. |
| 6,025,044 A | 2/2000 | Campbell et al. |
| 6,030,694 A | 2/2000 | Dolan et al. |
| 6,031,148 A | 2/2000 | Hayes et al. |
| 6,036,724 A | 3/2000 | Lentz et al. |
| 6,048,484 A | 4/2000 | House et al. |
| 6,066,776 A | 5/2000 | Goodwin et al. |
| 6,077,281 A | 6/2000 | Das |
| 6,080,182 A | 6/2000 | Shaw et al. |
| 6,080,198 A | 6/2000 | Lentz et al. |
| 6,080,472 A | 6/2000 | Huang et al. |
| 6,090,116 A | 7/2000 | D'Aversa et al. |
| 6,099,791 A | 8/2000 | Shannon et al. |
| 6,113,641 A | 9/2000 | Leroy et al. |
| 6,120,539 A | 9/2000 | Eldridge et al. |
| 6,133,165 A | 10/2000 | Tamaru et al. |
| 6,162,537 A | 12/2000 | Martin et al. |
| 6,162,962 A | 12/2000 | Hinsch et al. |
| 6,168,739 B1 | 1/2001 | Moeder |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,176,875 B1 | 1/2001 | Lenker et al. |
| 6,177,533 B1 | 1/2001 | Woodward |
| 6,187,043 B1 | 2/2001 | Ledergerber |
| 6,192,944 B1 | 2/2001 | Greenhalgh |
| 6,193,731 B1 | 2/2001 | Oppelt et al. |
| 6,210,439 B1 | 4/2001 | Firmin et al. |
| 6,214,020 B1 | 4/2001 | Mulhauser et al. |
| 6,214,029 B1 | 4/2001 | Thill et al. |
| 6,218,000 B1 | 4/2001 | Rudolf et al. |
| 6,224,616 B1 | 5/2001 | Kugel |
| 6,235,377 B1 | 5/2001 | Dillon et al. |
| 6,241,768 B1 | 6/2001 | Agarwal et al. |
| 6,258,124 B1 | 7/2001 | Darois et al. |
| 6,262,209 B1 | 7/2001 | Kapeliouchko et al. |
| 6,267,772 B1 | 7/2001 | Mulhauser et al. |
| 6,270,530 B1 | 8/2001 | Eldridge et al. |
| 6,274,043 B1 | 8/2001 | Newman et al. |
| 6,280,453 B1 | 8/2001 | Kugel et al. |
| 6,287,316 B1 | 9/2001 | Agarwal et al. |
| 6,287,337 B1 | 9/2001 | Martakos et al. |
| 6,287,497 B1 | 9/2001 | Kawachi et al. |
| 6,290,708 B1 | 9/2001 | Kugel et al. |
| 6,309,343 B1 | 10/2001 | Lentz et al. |
| 6,315,791 B1 | 11/2001 | Gingras et al. |
| 6,551,356 B2 * | 4/2003 | Rousseau ............... 623/23.72 |
| 6,652,595 B1 | 11/2003 | Nicolo |
| 6,669,735 B1 | 12/2003 | Pelissier |
| 6,790,213 B2 * | 9/2004 | Cherok et al. ............ 606/151 |
| 6,800,082 B2 * | 10/2004 | Rousseau ................. 606/151 |
| 2003/0078602 A1 | 4/2003 | Rousseau |

FOREIGN PATENT DOCUMENTS

| | | |
|---|---|---|
| DE | 29817682 U1 | 4/1999 |
| EP | 0194192 B2 | 9/1986 |
| EP | 0334046 A2 | 9/1989 |
| EP | 0358819 A1 | 3/1990 |
| EP | 0362113 A1 | 4/1990 |
| EP | 0474887 A1 | 3/1992 |
| EP | 0560934 B2 | 9/1993 |
| EP | 0719527 A1 | 7/1996 |
| EP | 0827724 A2 | 3/1998 |
| FR | 2744906 A1 | 8/1997 |
| GB | 1352282 | 5/1974 |
| GB | 1406271 | 9/1975 |
| RU | 1718857 A1 | 3/1992 |
| SU | 676285 | 7/1979 |
| SU | 782814 | 11/1980 |
| WO | WO 82/04390 | 12/1982 |
| WO | WO 88/01853 | 3/1988 |
| WO | WO 90/14796 | 12/1990 |
| WO | WO 92/10218 | 6/1992 |
| WO | WO 92/19162 | 11/1992 |
| WO | WO 93/17635 | 9/1993 |
| WO | WO 94/17747 | 8/1994 |
| WO | WO 96/09795 | 4/1996 |
| WO | WO 96/14805 | 5/1996 |
| WO | WO 97/21461 | 6/1997 |
| WO | WO 97/35533 | 10/1997 |
| WO | WO 98/14134 | 4/1998 |
| WO | WO 00/07520 | 2/2000 |
| WO | WO 02/22047 A1 | 3/2002 |

OTHER PUBLICATIONS

Johnson & Johnson "Prevention of postsurgical adhesions by Interceed (TC7), an absorbable adhesion barrier . . . " from Fertility and Sterility, Jun. 6, 1989 pp. 933-938.
Jenkins, et al "A comparison of prosthetic materials used to repair abdominal wall defects" from Surgery, Aug. 1983, pp. 392-398.
Uzzo, et al "The Effects of mesh bioprosthesis on the spermatic cord structures: A preliminary report in a canine model" from The Journal of Urology, Apr. 1999, pp. 1344-1349.
Walker, et al "Double-Layer Prostheses for Repair of Abdominal Wall Defects in a Rabbit Model", from Journal of Surgical Research, Jul. 1, 1993, pp. 32-37.
Cardona, "Prosthokreatoplasty" from Cornea, 1983 pp. 179-184.
European search report, dated Nov. 7, 2008, for European Patent Application No. 08165736.3.
Extended European Search Report, dated Feb. 3, 2010, for European Patent Application No. 09149038.6.

* cited by examiner

IMPLANTABLE PROSTHESIS

RELATED APPLICATIONS

This application is a continuation of U.S. application Ser. No. 10/040,936, filed Jan. 7, 2002, entitled IMPLANTABLE PROSTHESIS, now U.S. Pat. No. 6,790,213, which is herein incorporated by reference in its entirety.

FIELD OF INVENTION

The present invention relates to an implantable prosthesis and, more particularly, to a prosthesis for soft tissue or muscle defects.

DISCUSSION OF RELATED ART

Various prosthetic materials are used to repair and/or reinforce anatomical defects, such as tissue and muscle wall hernias. For example, ventral and inguinal hernias are commonly repaired using a sheet of biocompatible fabric, such as a knitted polypropylene mesh (BARD MESH). Tissue integration with the fabric, such as by tissue ingrowth into the fabric, eventually completes the repair.

In certain procedures, the prosthetic fabric may come into contact with tissue or organs potentially leading to undesirable postoperative adhesions and undesirable tissue attachment between the mesh and the tissue or organs. To avoid such adhesions, a prosthesis that is covered with an adhesion resistant barrier may be used. In the repair of ventral hernias, the prosthesis is positioned with the barrier facing the region of potential adhesion, such as the abdominal viscera. In the case of chest wall reconstruction, the barrier faces the thoracic viscera (i.e., heart and lungs). One example of such a prosthesis is disclosed in U.S. Pat. No. 5,593,441, assigned to C.R. Bard, Inc. Another example of a prosthetic material including an adhesion resistant barrier is disclosed in U.S. Pat. No. 6,120,539, also assigned to C.R. Bard, Inc.

Once inserted into a patient, the prosthesis is typically sutured, stapled or otherwise provisionally anchored in place over, under or within the defect. In some prostheses, such as that described in U.S. Pat. No. 6,267,772, also assigned to C.R. Bard, Inc., antimigration barbs extend from the implantable material to prevent migration of the prosthesis after implantation.

Another issue that is of concern is the correction of defects which occur in tissue or muscle weakened by previous surgery or large defects in tissue or muscle of obese patients. Factors such as obesity, chronic pulmonary disease, prior surgery, wound infection and seroma or hematoma formation continue to exert adverse influences on wound healing and increase the chance of recurrent herniation. Often, the abdominal wall of these patients is severely compromised and weakened such that it will not support a primary correction, and any such closure may be associated with a significant recurrence rate. Other configurations of prostheses can be found in U.S. Pat. Nos. 5,695,525; 5,725,577, 5,743,917, and 6,267,772, each of which is also assigned to C. R. Bard, Inc.

SUMMARY OF THE INVENTION

The present invention relates to an implantable prosthesis for an anatomical defect, such as a tissue or muscle defect, that promotes tissue growth into the prosthesis and subsequently strengthens the area of the defect. The prosthesis is easy to manipulate and is designed to minimize the incidence of postoperative adhesions between a portion of the prosthesis and surrounding tissue or organs. In addition, the prosthesis strikes a balance between being sufficiently rigid to aid in manipulation and deployment in the area of desired coverage and sufficiently flexible to be acceptable to both the surgeon and the patient. Further, the prosthesis is constructed to allow it to be provisionally held in place at desired locations until sufficient tissue ingrowth occurs. Embodiments of the prosthesis are particularly suited for correction or repair of large defects, such as those that may occur in obese patients. The prosthesis may include one or more features, each independently or in combination, contributing to such attributes.

In one embodiment, an implantable prosthesis for a tissue or muscle defect includes first and second layers of material that permit the formation of adhesions with tissue or muscle. The second layer is attached to the first layer. At least one pocket is formed between the first and second layers. A layer of barrier material that is resistant to the formation of adhesions with tissue or muscle is attached to at least the second layer.

In one aspect of this embodiment, substantial areas of the second layer are free from attachment to the layer of barrier material. In another aspect, the prosthesis is constructed and arranged to be provisionally attached to the tissue or muscle. In other aspects, the layer of barrier material includes ePTFE and, each of the first and second layers comprises polypropylene mesh.

In another embodiment, an implantable prosthesis for a tissue or muscle defect includes at least one layer of material, at least a portion of which permits the formation of adhesions with tissue or muscle. The at least one layer includes a peripheral edge, an outer area disposed inwardly of the peripheral edge, and an inner area disposed inwardly of the outer area. A pocket is formed in the at least one layer. A first reinforcing member is coupled to the at least one layer, surrounds the outer area and is constructed and arranged to reinforce at least the outer area. A second reinforcing member is inwardly spaced from the first reinforcing member and is coupled to the at least one layer.

In one aspect of this embodiment, each of the first and second reinforcing members is formed in a ring-shaped configuration and in another aspect, the first and second reinforcing members are generally concentric with each other. In yet another aspect, the first and second reinforcing members are sandwiched between first and second layers of material and in still another aspect, the first and second layers of material are stitched together to form a first channel and a second channel, with the first reinforcing member being disposed within the first channel and the second reinforcing member being disposed in the second channel. In yet another aspect, at least a portion of the outer area is constructed and arranged to extend beyond the defect by at least approximately 3 cm, and in still another aspect, the prosthesis includes a surface having an area greater than 50 square cm.

In yet another embodiment, an implantable prosthesis for a tissue or muscle defect includes at least one layer of material, at least a portion of which permits the formation of adhesions with tissue or muscle. The at least one layer includes a peripheral edge, an outer area disposed inwardly of the peripheral edge and an inner area disposed inwardly of the outer area. At least one first pocket is formed in the inner area and at least one second pocket is formed in the outer area separately from the at least one first pocket. The at least one second pocket includes at least one access opening for gaining access to an interior of the at least one second pocket.

In one aspect of this embodiment, the prosthesis includes a partition closing an end of the first pocket and defining a boundary between the at least one first pocket and the at least one second pocket. In another aspect, the partition is constructed and arranged to prevent access from the first pocket to the second pocket. In yet another aspect, the at least one access opening comprises a plurality of spaced openings. In still another aspect, the spaced openings are formed in the first layer of material and in still another aspect, a portion of the first layer of material between the plurality of openings forms a bridge to the inner area. In another aspect, the at least one first pocket is constructed and arranged to receive four fingers of a person implanting the prosthesis.

In still another embodiment, an implantable prosthesis for a tissue or muscle defect includes at least one layer of material, at least a portion of which is susceptible to the formation of adhesions with tissue or muscle. The at least one layer of material includes a first layer of mesh material and a second layer of mesh material attached to the first layer of mesh material. The at least one layer includes a peripheral edge, an outer area disposed inwardly of the peripheral edge and an inner area disposed inwardly of the outer area. At least one first pocket is formed in the inner area and is defined by attachment of the first and second layers of mesh material. At least one second pocket is formed in the outer area and is defined by attachment of the first and second layers of mesh material. The at least one second pocket is separate from the at least one first pocket. Each of the at least one first and second pockets includes an access opening for gaining access to an interior of the respective at least one pocket. A first reinforcing member is coupled to the at least one layer, substantially surrounds the outer area and is constructed and arranged to reinforce at least the outer area. A second reinforcing member is inwardly spaced from the first reinforcing member and is coupled to the at least one layer.

In another embodiment, an implantable prosthesis for a tissue or muscle defect includes at least one layer of material, at least a portion of which is susceptible to the formation of adhesions with tissue or muscle. The at least one layer of material includes a first layer of mesh material and a second layer of mesh material attached to the first layer of mesh material. The at least one layer includes a peripheral edge, an outer area disposed inwardly of the peripheral edge and an inner area disposed inwardly of the outer area. A barrier layer that substantially inhibits the formation of adhesions with tissue is attached to at least the second layer of mesh material. At least one first pocket is formed in the inner area and is defined by attachment of the first and second layers of mesh material. At least one second pocket is formed in the outer area and is defined by attachment of the first and second layers of mesh material. The at least one second pocket is separate from the at least one first pocket. Each of the at least one first and second pockets includes an access opening for gaining access to an interior of the respective at least one pocket. A first reinforcing member is coupled to the at least one layer, substantially surrounds the outer area and is constructed and arranged to reinforce at least the outer area. A second reinforcing member is inwardly spaced from the first reinforcing member and is coupled to the at least one layer.

Various embodiments of the present invention provide certain advantages and overcome certain drawbacks of prior prostheses. Embodiments of the invention may not share the same advantages, and those that do may not share them under all circumstances. This being said, the present invention provides numerous advantages including the noted advantages of ease of implantation and promotion of desired tissue or muscle growth without involving surrounding tissue or organs.

Further features and advantages of the present invention, as well as the structure of various embodiments, are described in detail below with reference to the accompanying drawings.

BRIEF DESCRIPTION OF THE DRAWINGS

Various embodiments of the invention will now be described, by way of example, with reference to the accompanying drawings, in which.

DESCRIPTION OF ILLUSTRATIVE EMBODIMENTS

Figure 1:
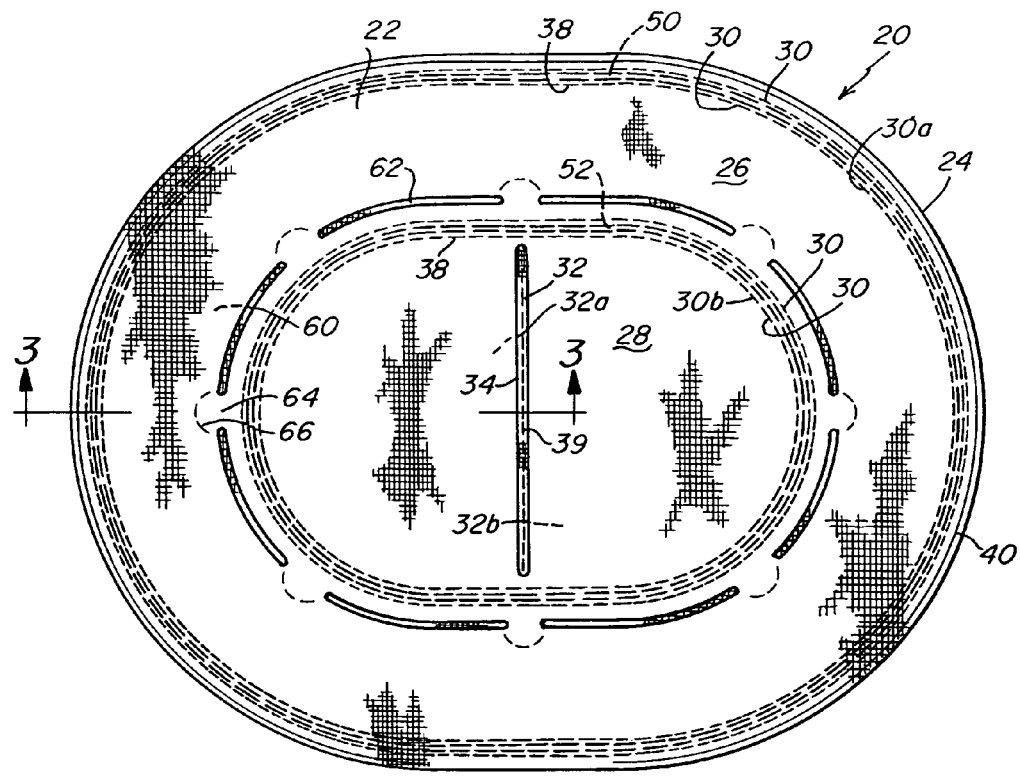
FIG. 1 is a top plan view of an implantable prosthesis in accordance with one illustrative embodiment of the present invention.
Figure 2:
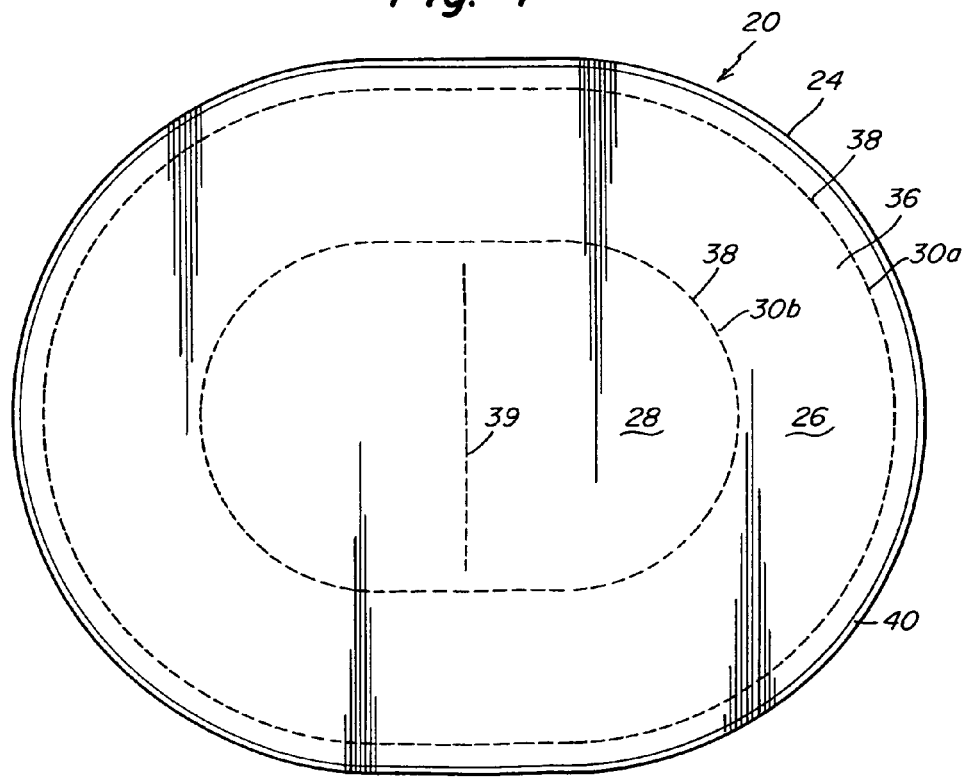
FIG. 2 is a bottom plan view of the prosthesis of FIG. 1.

An implantable prosthesis for an anatomical defect, such as a tissue or muscle defect, that promotes tissue or muscle growth into the prosthesis and subsequently strengthens the area of the defect is provided. The incidence of postoperative adhesions between a portion of the prosthesis and surrounding tissue or organs may be minimized. The prosthesis is easy to manipulate and properly deploy in the area of desired coverage (e.g., over, under or within the defect). In addition, the prosthesis is constructed to allow it to be provisionally held in place until sufficient tissue or muscle ingrowth occurs, without compromising the integrity or strength of the prosthesis. To achieve these and other attributes, the prosthesis includes various features, each of which will be described in greater detail below, that may be employed singularly or in any suitable combination.

FIGS. 1-7 illustrate embodiments of such an implantable prosthesis for correcting soft tissue or muscle defects. The prosthesis 20 includes an ingrowth layer 22 of tissue infiltratable material. The ingrowth layer 22 includes a peripheral edge 24, an outer peripheral area 26 disposed inwardly of the peripheral edge 24 and an inner central area 28 disposed inwardly of and surrounded by the outer peripheral area 26. The ingrowth layer 22 includes at least one layer of material 22a that permits or is otherwise susceptible to tissue or muscle adhesions. In one embodiment, the ingrowth layer 22 includes first and second layers 22a, 22b joined together. Each layer 22a, 22b is formed of a biologically compatible, flexible material that includes a plurality of interstices or openings which allow sufficient tissue or muscle ingrowth to secure the prosthesis to host tissue or muscle after implantation.

In one embodiment, each layer 22a, 22b is formed of a sheet of knitted polypropylene monofilament mesh fabric such as BARD MESH available from C.R. Bard, Inc. When implanted, the polypropylene mesh promotes rapid tissue or muscle ingrowth into and around the mesh structure. Alternatively, other surgical materials which are suitable for tissue or muscle reinforcement and defect correction may be utilized including SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Absorbable materials, including polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the prosthetic mesh material.

To ensure that adequate tissue or muscle ingrowth occurs, the two layers of material are attached only in a way that would permit tissue to grow into the pores of layer 22b and provide a strong bond between the surrounding muscle or tissue and layer 22b. Preferably, layers 22a and 22b are not laminated or bonded to each other over the entire surface of layer 22b. Also, preferably, layers 22a and 22b are not bonded using an adhesive that would fill a large number of the pores of the layers 22a and 22b or by a method that would otherwise compromise the porosity of layers, such by melting. In one embodiment, the first and second layers 22a, 22b are connected with stitches 30.

Figure 4:
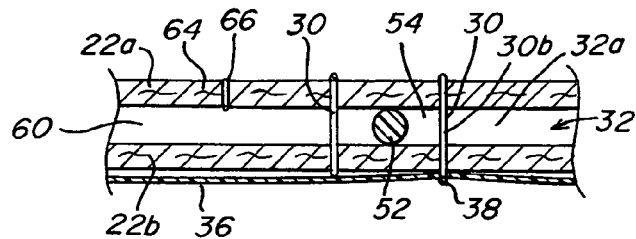
FIG. 4 is an enlarged view of the area encircled by line 4 of FIG. 3.

In one embodiment, layers 22a and 22b are attached only at discrete locations (see FIG. 4). In this manner, tissue or muscle is able to grow through the first layer 22a and into the second layer 22b. Although a single stitch line 30 may adequately secure the ingrowth layers together, it may be desirable to use additional stitch lines to limit the amount of billowing of the ingrowth layers 22a and 22b. In addition, although the attachment is shown to include concentric patterns, any suitable pattern may be employed so as to minimize separation of the layers.

It should be appreciated that the invention is not limited to any particular attachment method, as the first and second layers may be attached using other suitable techniques. For example, the layers may be bonded together by melting the layers at specific locations or in a specified pattern; sonic, induction, vibration, or infrared/laser welding the layers; or using a suitable bonding agent. The point or points of attachment may comprise any suitable pattern, such as a spiral pattern, a serpentine pattern or a grid-like pattern of dots or beads, that maintains a sufficient quantity of open or non-impregnated interstices for tissue or muscle infiltration.

To aid in positioning and/or provisionally attaching the prosthesis, the prosthesis includes a pocket 32. In this manner, a surgeon may use the pocket to position the prosthesis in the desired area. Thereafter, the surgeon may suture or staple one of the layers of material to the surrounding ingrowth tissue, muscle or peritoneum layer. For example, the surgeon may enter the pocket and suture or staple the upper layer of the pocket to the tissue, muscle or peritoneum layer. As such, the prosthesis may be provisionally held in place at least until sufficient tissue or muscle ingrowth occurs. In one embodiment, the first and second layers are attached in a manner to form the pocket 32 therebetween. However, it should be appreciated that the invention is not limited in this respect and that a pocket 32 need not be employed or that other suitable pockets formed in other suitable manners may be employed.

For example, a pocket may be formed from an additional layer of material or portion thereof attached to the first layer 22a.

To gain access to the interior of the pocket, the pocket 32 includes an opening 34. In one embodiment, the opening is a transverse cut or slit formed in the first layer 22a. To position the prosthesis, the surgeon inserts one or more fingers (or a suitable surgical instrument) into the pocket and manipulates the prosthesis into place. In one embodiment, the pocket 32 is sized to accept at least four fingers of the surgeon's hand, although other suitably sized pockets may be employed, as the present invention is not limited in this respect. Further, the pocket 32 may be formed of multiple pockets so that one or more fingers may be inserted into individual finger sections. In the embodiment shown, the pocket 32 includes a first side pocket 32a and a second side pocket 32b (see FIGS. 1 and 7). However, it should be appreciated that the invention is not limited in this respect and that only a single side pocket may be employed.

In certain procedures, such as in the correction of ventral hernias or in the reconstruction of chest or abdominal walls, the ingrowth layer may come into contact with tissue, muscle or organs, which is not intended to grow into the ingrowth layer. Such contact could potentially lead to undesirable postoperative adhesions between the ingrowth layer and the surrounding tissue, muscle or organs. To minimize or eliminate the incidence of postoperative adhesions to selected portions of the prosthesis, the prosthesis may include a tissue, muscle or organ adhesion resistant barrier layer 36 overlying at least a portion, and preferably all, of one side of the ingrowth layer 22. In one embodiment, the barrier layer 36 is attached to the prosthesis on the side adjacent to the second layer 22b. The prosthesis 20 is positioned in a patient such that the barrier layer 36 faces the region of potential undesired adhesion, such as the abdominal viscera (e.g., intestines) or the thoracic viscera (e.g., heart or lungs). As will be discussed in more detail below, the barrier layer 36 is formed of a material and/or with a structure that does not substantially stimulate and in fact resists tissue, muscle or organ ingrowth and adhesion formation when implanted, thereby limiting or completely eliminating the incidence of undesired postoperative adhesions between the ingrowth layer and adjacent tissue, muscle or organs.

In one embodiment, the barrier layer 36 is formed from a sheet of expanded polytetrafluoroethylene (ePTFE) having fibril lengths—also referred to as pore size or internodal distance—that will not permit significant tissue ingrowth. In one embodiment, the fibril lengths of the ePTFE are less than 5 microns. In another embodiment, the fibril lengths of the ePTFE are less than 1 micron and in still another embodiment, the fibril lengths are less than 0.5 microns. Examples of other suitable materials for forming the barrier layer 36 include FLUORO-TEX Pericardial and Peritoneum Surgical Membrane and FLUORO-TEX Dura Substitute available from C.R. Bard and PRECLUDE Pericardial Membrane, PRECLUDE Peritoneal Membrane and PRECLUDE Dura Substitute membrane available from W.L. Gore & Associates, Inc. A representative and non-limiting sampling of other suitable micro to non-porous materials includes silicone elastomer, such as SILASTIC Rx Medical Grade Sheeting (Platinum Cured) distributed by Dow Corning Corporation, and microporous polypropylene sheeting (available from Celgard, Inc.) and film. Autogenous, heterogenous and xenogeneic tissue also are contemplated including, for example, pericardium and small intestine submucosa. Absorbable materials, such as SEPRAFILM available from Genzyme Corporation and oxidized, regenerated cellulose (Intercede (TC7)) may be employed for some applications. It is to be appreciated that other suitable biocompatible adhesion resistant materials also may be used.

The prosthesis 20 may be particularly useful in correcting tissue defects where conventional tissue approximation is not feasible, for example, the correction of a large defect, such as a large incisional hernia, particularly one which occurs in tissue or muscle weakened by previous surgery or in tissue or muscle of obese patients. For this purpose, prosthesis 20 bridges the defect and supports the surrounding tissue or muscle as the tissue or muscle grows into the ingrowth layer and after such ingrowth occurs. In one embodiment, to support stresses induced by the patient (e.g., by patient movements), thereby limiting recurrent defects, it is desirable that the tissue or muscle be able to grow into the layer of ingrowth material that is best suited for supporting such stresses. Since layer 22a includes at least one opening 34, it is relatively less able to support the required stress. On the other hand, the second layer 22b includes no sizable openings, or other large discontinuities, and is generally uniform and is therefore more able to support the required load. Therefore, in the embodiment described herein, the load bearing layer is layer 22b.

It should be appreciated that the present invention is not limited in this respect and that the prosthesis 20 may be formed with suitably sized and shaped openings or discontinuities in the second layer 22b, provided such openings or discontinuities do not reduce the load bearing ability of the second layer beyond a tolerable amount. For example, a relatively smaller prosthesis may employ such openings or discontinuities. These openings or discontinuities may be used to help at least provisionally anchor the prosthesis and promote tissue ingrowth. Examples of prosthesis employing such openings and discontinuities are descried in U.S. Pat. Nos. 6,290,708 and 6,224,616, which are assigned to the assignee of the present invention and which are here by incorporated by reference in their entireties.

To permit and facilitate tissue or muscle growth into the second layer 22b, the barrier layer 36 preferably is attached to the second layer 22b only in a way that would permit tissue to grow into the pores of layer 22b and provide a strong bond between the surrounding muscle or tissue and layer 22b. Preferably, layer 22b is not laminated to the barrier layer 36 and is not bonded to the barrier layer 36 over the entire surface of layer 22b. Also, preferably, layer 22b is not bonded to the barrier layer 36 using an adhesive that would fill a large number of the pores of layer 22b or by a method that would otherwise compromise the porosity of layer 22b, such by melting.

In one embodiment, as shown in FIGS. 1-5, the first and second layers 22a, 22b are attached together at discrete attachment lines, using stitches which allow sufficient tissue infiltration to the ingrowth layer, and in particular, layer 22b, while providing a connection between layers 22a and 22b. In addition, these same stitches (e.g., stitches 38) may be used to secure layer 22b to barrier layer 36. Although stitch lines 38 may adequately secure the barrier layer 36 to the ingrowth layer 22b, it may be desirable to use additional stitch lines, such as stitch line 39, to limit the amount of billowing of the barrier layer away from the ingrowth layer. Although the attachment is shown to include concentric patterns, any suitable pattern may be employed so as to minimize separation of the ingrowth layer and the barrier layer.

Figure 5:
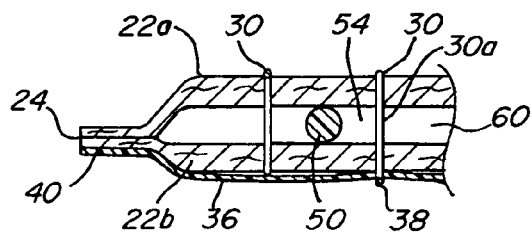
FIG. 5 is an enlarged view of the area encircled by line 5 of FIG. 3.

On the other hand, different sets of stitches may be used to secure layers 22a and 22b together than one used to secure layer 22b to layer 36. For example, as shown in FIGS. 4 and 5, not all stitch lines 30 pass through the barrier layer 36. Rather, only stitch lines 38 pass through the barrier layer 36. It is preferred that as few stitches as necessary to secure layer 36 to layer 22b are employed so that tissue or muscle adhesion on the barrier layer side of the prosthesis is minimized. Also, in the embodiment shown, center stitch line 39 passes only through the second layer 22b and the barrier layer 36, as the first layer 22a includes the access opening 32 at that location.

Although, in one embodiment, the barrier layer 36 is attached to the ingrowth layer 22b with stitches, it should be appreciated that the invention is not limited in this respect, as the barrier layer may be attached using other suitable techniques. For example, the barrier layer may be bonded to the ingrowth layer by heating the layers, welding the layers, or using a suitable bonding agent. In either case, a suitable pattern, such as a spiral pattern, a serpentine pattern or a grid-like pattern of dots or beads may be used, provided a sufficient quantity of open or non-impregnated interstices is maintained in at least layer 22b for tissue or muscle infiltration.

Where stitches are employed to attach the ingrowth layer 22b to the barrier layer 36, to further minimize adhesions, the stitches may be formed from a non-porous, adhesion resistant material. For example, the stitches may be formed with a suitable polytetrafluoroethylene (PTFE) monofilament. PTFE stitches may provide a softer, more flexible prosthesis that is easier to manipulate as compared to a prosthesis using other stitch materials, such as polypropylene monofilament. PTFE monofilament also facilitates the manufacturing process due to the low friction characteristics of the material. Nevertheless, it should be understood that any suitable material, such as polypropylene monofilament, may be employed for the stitches. For example, because some of the stitch lines do not pass through the barrier layer, or where no barrier layer is employed, materials other than an adhesion resistant material may be employed. For ease of manufacturing however, typically, all stitches are formed of the same material, although the invention is not limited in this respect.

The layers may be stitched using a typical sewing stitch formed by a sewing machine using a bobbin and sewing thread. Preferably, the barrier layer is positioned on the ingrowth layer to face the sewing needle so that the locking portion of each stitch (i.e. the bobbin) is formed on the ingrowth side of the prosthesis rather than on the barrier side to reduce the incidence of localized adhesions with tissue, muscle or organs. The stitches may be formed using a #10 ball-tipped needle to reduce the potential incidence of ingrowth through the stitch holes. The sheets of ingrowth material with or without the barrier layer may be held by a frame during the sewing procedure on a computer controlled table that has been programmed with the desired stitch pattern.

While preferably the barrier layer 36 covers the entire surface of one side of the ingrowth layer 22, barrier layer 36 may be configured to cover only selected portions of one side of the prosthesis to enhance ingrowth from both sides in those portions free of the barrier layer. Similarly, the prosthesis may be configured such that the barrier layer covers the entire surface on one side of the prosthesis and covers one or more portions of the other side of the prosthesis.

In some instances, it may be desirable to isolate the outer peripheral edge of the prosthesis 20 from adjacent tissue, muscle or organs. In one embodiment, a peripheral barrier 40 (see FIGS. 1, 3 and 5) extends completely about the outer peripheral edge 24 of the prosthesis 20 to inhibit adhesions thereto. It is to be understood, however, that the peripheral barrier 40 may be configured to cover only those selected portions of the outer peripheral edge of the prosthesis where protection from the formation of postoperative adhesions is desired.

The peripheral barrier 40 may be formed integrally with either the ingrowth layer 22 or the barrier layer 36. Alternatively, the peripheral barrier 40 may be formed by a separate component that is attached to or incorporated into the outer peripheral edge of the prosthesis. In one illustrative embodiment, the peripheral barrier 40 is formed from a portion of the ingrowth layer 22. In particular, the ingrowth layer 22 may be altered so as to substantially eliminate the tissue infiltratable interstices or openings along its outer margin, thereby creating a peripheral barrier 40.

Figure 3:
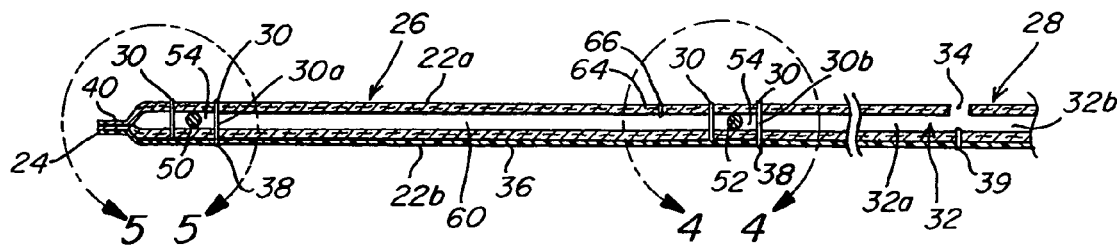
FIG. 3 is a cross-sectional view of a portion of the prosthesis taken along section line 3-3 of FIG. 1.

In one embodiment, as shown in FIGS. 3 and 5, the peripheral edge 24 of layers 22 is melted to seal the material and form an outer peripheral barrier 40. The barrier layer 36 may be configured, such as with submicronal sized pores, so that a portion of the melted material of layer 22 becomes fused to the barrier layer 36. The peripheral edge 24 may be melted using any suitable process. In one embodiment, the peripheral edge 24 may be melted by heat sealing the layer. In the exemplary embodiment, the peripheral barrier 40 is formed by melting a ring of polypropylene mesh fabric to the ePTFE barrier layer 36 in a shape that approximates the desired configuration of the prosthesis. This may be accomplished by overlying oversized sheets of the mesh fabric and ePTFE material in a fixture and heat sealing the layers using a heated die configured with the desired shape of the prosthesis. The melted ring may be formed by applying heat to the fabric at a temperature range of approximately 320° F. to 400° F. for a period of approximately 3 to 5 seconds. The temperature chosen typically should be below the sintering temperature of the ePTFE barrier layer. Other sealing techniques may be used, such as ultrasonic, induction, vibration, infrared/laser welding and the like, as the present invention is not limited in this respect. Once fused, the ingrowth layer is stitched to the barrier layer, as described above, and subsequently die cut flush along a portion of the ring to complete the prosthesis with a peripheral barrier.

Other suitable techniques for creating a peripheral barrier may be employed, as the present invention is not limited in this respect. Examples of such other techniques are described in copending U.S. application Ser. No. 09/661,623, which is assigned to the assignee of the present invention and which is hereby incorporated by reference in its entirety.

Although some embodiments described above include a barrier layer, the present invention is not limited in this respect. Thus, other embodiments, such as those that will be described below may or may not include the barrier layer or the peripheral barrier.

In some instances, such as (but not limited to) the correction of relatively large defects, it may be desirable to employ a prosthesis that is sufficiently rigid so that it can be easily and effectively manipulated and positioned in the desired area yet sufficiently flexible so that the prosthesis is adequately tolerated by both the physician implanting the prosthesis and the patient receiving the prosthesis. The prosthesis should conform to the shape of the area being covered and should be sufficiently rigid such that the edges do not excessively curl. This attribute may be particularly useful with a large prosthesis sized for use with large defects in obese patients. Thus, according to another aspect of the invention, to balance the stiffness and flexibility, the prosthesis 20 includes a first reinforcing member 50 and a separate second reinforcing member 52 inwardly spaced from the first reinforcing member.

The reinforcing members 50, 52 may be coupled to the ingrowth layer 22 in any suitable manner, as will be described in more detail below.

The reinforcing members contribute to the stability of the prosthesis, allowing it to remain in a desired shape. For example, the reinforcing members aid in allowing the prosthesis to remain substantially planar. This stability facilitates deployment and placement of the prosthesis by making it easy to handle. Also, the stability minimizes the tendency of the prosthesis to sag, fold, bend or otherwise become dislocated. Difficulty in handling or dislocation or bending could require additional operative procedures and/or additional anchoring during implantation. As will be discussed below, during implantation of the prosthesis, sutures may be passed around the reinforcing members to maintain the prosthesis in generally the desired configuration and location.

In one embodiment, the first reinforcing member 50 is substantially continuous and surrounds the outer area 26 of the prosthesis to reinforce at least the outer area 26. In the embodiment shown in the figures, the reinforcing member 50 is not disposed at the peripheral edge 24. Rather, the reinforcing member 50 is spaced inwardly of the peripheral edge 24. However, it should be appreciated that the present invention is not limited in this respect, as the reinforcing member 50 may be disposed at the peripheral edge 24.

The second reinforcing member 52 is disposed inwardly of the first reinforcing member and may be employed to reinforce the inner area 28 of the prosthesis. In one embodiment, the second reinforcing member is continuous and extends around the inner area 28 and defines the outer perimeter of pocket 32. In the embodiment shown, each reinforcing member 50 and 52 is a monofilament thread of a desired thickness and cross-sectional shape and configured on the prosthesis in the shape of a ring. It should be appreciated that the reinforcing members may have any cross-sectional shape, such as circular, square, rectangular, triangular, elliptical, etc. Members 50 and 52 may be configured on prosthesis 20 in any pattern, such as a spiral pattern, a square pattern, an elliptical pattern, a circular pattern or the like.

In the embodiment shown, the second, inner reinforcing member 52 is concentric or generally concentric with the first, outer reinforcing member 50. However, it should be appreciated that the invention is not limited in this respect as other suitable arrangements may be employed.

Typically, the second, inner reinforcing member 52 is positioned on the prosthesis such that it will generally align with the edges of the defect when the prosthesis is implanted. In this manner, during implantation, sutures may be passed around or near the second, inner reinforcing member 52, and used to provisionally attach inner area 26 to the tissue or muscle near the edges of the defect. Also, sutures may be passed around or near the first, outer reinforcing member 50 and also attached to the tissue or muscle farther away from the edges of the defect, typically between 3 cm and 5 cm away from the edge of the defect, so that the outer area 26 may also be provisionally attached to the tissue or muscle.

The reinforcing members 50, 52 may be disposed on the prosthesis in any suitable manner as the present invention is not limited in this respect. In one embodiment, as shown in FIGS. 3-5, the first and second reinforcing members 50, 52 are sandwiched between the first and second layers of ingrowth material 22a, 22b and may or may not be physically attached thereto. The reinforcing members may be tightly or loosely held within channels 54 formed by the attachment of the first and second layers 22a, 22b at attachment lines 30, such as stitch lines. A single line 30 formed by sewing threads typically is stitched at least along the outside or inside edge of members 50 and 52 to keep them from moving with respect to layers 22a and 22b. Because of the rigidity of members 50 and 52, one stitching line along one side of members 50 and 52 may be enough. However, preferably, there are two stitching lines, one on either side of each members 50 and 52 to hold them in place by forming the channels 54 in which they reside. Preferably, these stitches extend through both of layers 22a and 22b, but not through barrier layer 36, if it is present. Another advantage is that member 50, if stitched or bonded to layer 36 or to layers 22a and 22b, holds the layers 22a, 22b and/or layer 36 together in a manner to prevent billowing of layer 36 with respect to layer 22 or layers 22a and 22b with respect to each other.

Alternatively, the reinforcing members 50, 52 may overlie or underlie the ingrowth layer 22 and may be attached, regardless of location, with stitches or a bonding agent, or fused by ultrasonic, induction, vibration, infrared/laser welding and the like. Alternatively, the reinforcing members may be woven through at least one of the layers 22a, 22b or integrally formed with the layer 22 as the layer 22 itself is being made. In instances where a barrier layer is employed, it is desirable that the reinforcing members 50, 52 are not positioned under the barrier layer 36 or protrude therethrough, as doing so may result in undesirable adhesions forming on the reinforcing members.

Although the reinforcing members 50, 52 are described as being formed of a monofilament thread, other suitable constructions may be employed. For example, the reinforcing members may be molded elements that are subsequently attached to the prosthesis or molded onto the prosthesis. An example includes the ring shown in U.S. Pat. No. 5,695,525 which is incorporated herein by reference. In addition, the reinforcing elements may be formed from the ingrowth layer. In this respect, each reinforcing member 50, 52 may be formed by melting a portion of the ingrowth layer 22 in any desired shape. The reinforcing members may be formed by applying heat to the ingrowth layer at a temperature range of approximately 320° F. to 400° F. for a period of approximately 3 to 5 seconds. In another example, the reinforcing members 50, 52 may be formed of multiple stitches passing through one or both layers 22a and 22b, such as, for example, an embroidered section. Alternatively, the reinforcing members 50, 52 may be formed by altering the weave pattern in the zone of desired reinforcement. In this manner, the area of the ingrowth layer 22 where tissue ingrowth is desired is formed with a relatively loose or open weave whereas the area or zone of reinforcement is formed with a relatively tight weave to provide the desired rigidity. Other suitable methods or mechanisms to form the reinforcing members 50, 52 may be employed, as the present invention is not limited in this respect.

In one embodiment, portions of the prosthesis may include anchoring elements used to provisionally hold the prosthesis in place. These anchoring elements may be in addition to or instead of sutures, staples or tacks. In one embodiment, anchoring elements may be attached or otherwise formed on the reinforcing members. Examples of such anchoring elements are described in U.S. Pat. No. 6,267,772, which is assigned to the assignee of the present invention and which is hereby incorporated by reference in its entirety.

Although some embodiments described above include reinforcing members, the present invention is not limited in this respect. Thus, other embodiments, such as those that will be described below may or may not include the reinforcing members.

As discussed above, after the prosthesis is inserted in position, or during implantation, a portion of the prosthesis may become dislocated prior to the occurrence of sufficient tissue or muscle ingrowth. For example, the outer region of the prosthesis may become folded or otherwise move and become susceptible to undesirable tissue, muscle or organ adhesions. This dislocation or folding is a particular problem for a relatively large prosthesis, such as for large defects in obese people, where the defect, and subsequently area 26, is quite large. To lessen this possibility, the outer edge of the prosthesis is provisionally held in place with the use of sutures, staples, helical tacks or other suitable anchors. Thus, according to another embodiment, the prosthesis includes a pocket 60 formed in the outer peripheral area 26 of the prosthesis beyond pocket 32. Pocket 60 may be used to manipulate the prosthesis and to provisionally anchor outer area 26, as will be described. Pocket 60 is sized to accept at least a portion of the surgeon's hand or a suitable surgical instrument to permit manipulation of outer area 26 to ensure that the prosthesis is lying in the correct orientation and generally is positioned in the proper location. Further, the pocket is sized to accept a suitable instrument, such as an instrument that deploys sutures, staples, helical tacks or other anchors, so that the surgeon may properly anchor the outer area 26 to the surrounding ingrowth tissue, muscle or peritoneum layer.

Like the first pocket 32, in one embodiment, the second pocket 60 is defined by attachment of the first and second layers 22a, 22b. In particular, the first and second layers 22a, 22b are joined together at discrete locations to form the pocket 60. However, the invention is not limited in this respect as the second pocket may be formed on the prosthesis in any suitable manner. For example, the second pocket 60 may be formed with an additional layer of material (not shown) attached to the top surface of the prosthesis.

In one embodiment, the second pocket 60 is constructed to extend substantially to the peripheral edge 24. Where a member 50 is used, the second pocket 60 extends to reinforcing member 50. If member 50 is held in place by stitches, pocket 60 typically extends to attachment line 30a (see FIGS. 1, 3 and 5), such that attachment line 30a defines the outer periphery of the second pocket 60. In addition, member 52 defines a boundary between pockets 32 and 60 such that access to the second pocket 60 from the first pocket 32 is prevented.

A benefit to providing a barrier or partition between the first and second pockets is that the prosthesis is easier to implant. In this respect, when the prosthesis is relatively large, the surgeon may maneuver the prosthesis into position without having to insert his or her hand or a tool all the way into pocket 60 to push against the peripheral edge 24. Rather, the surgeon's hand or tool can enter the center pocket 32 through slit 34 and push against the partition or barrier (e.g., member 52 or stitch line 30b) to move the prosthesis into place.

Because the two pockets 32 and 60 are separate, second pocket 60 is provided with its own opening 62 to permit access into the interior of pocket 60. In one embodiment, the access opening 62 is in the form of a cut or slit in the first layer 22a, which may be sized and shaped to accept at least a portion of the surgeon's hand or one or more suitable surgical instruments. The opening may be arcuately shaped and in one example, has a length, as measured along the arc, of about 6.5 cm. Of course, other suitably sized and shaped openings may be employed as the present invention is not limited in this respect.

Gaining access to the interior of second pocket 60 may also be helpful when provisionally attaching the prosthesis. Stapling or suturing devices (not shown) may be inserted into pocket 60 through opening 62 so that, sutures, staples, helical tacks or other anchors may be positioned through the second pocket to provisionally attach at least the outer portion of the prosthesis to the surrounding tissue or muscle.

Figure 7:
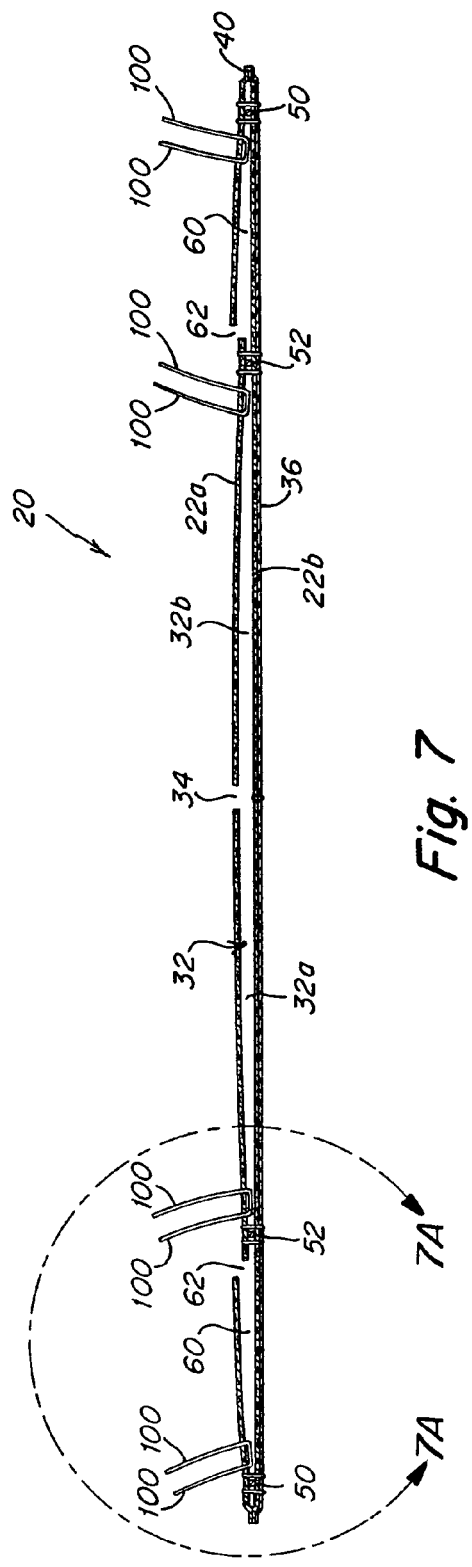
FIG. 7 is a cross-sectional view of the prosthesis of FIG. 1 showing provisional anchoring of the prosthesis.
Figure 7A:
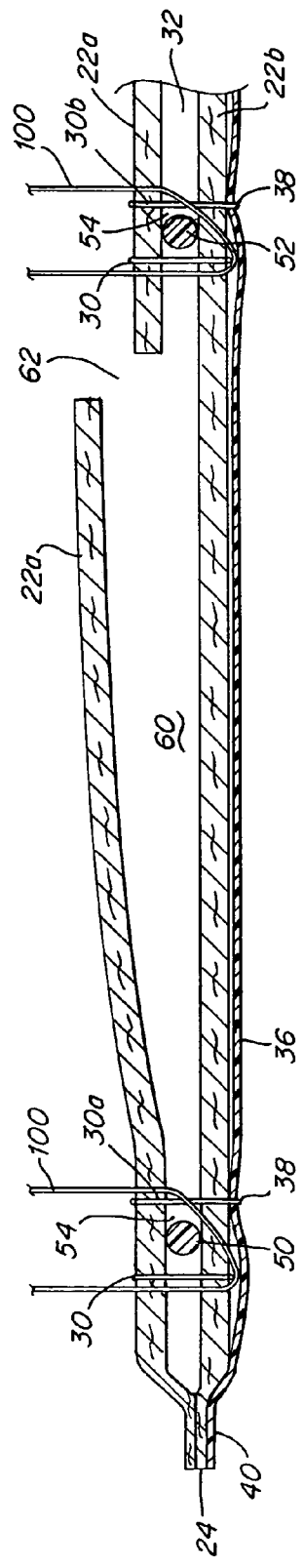
FIG. 7A is enlarged view of the area encircled by line 7A of FIG. 7 showing an alternative technique for provisionally anchoring of the prosthesis.

Preferably, although not necessary, the prosthesis is attached to the tissue or muscle at a location close to the edges of the defect and also at a location close to the edge of the prosthesis. The prosthesis may be secured in any suitable manner, as the present invention is not limited in this respect. In one embodiment, sutures may be used. For example, as shown in FIG. 7, when using sutures, prior to introduction of the prosthesis into the patient, sutures 100 may be passed through one or both ingrowth layers 22a and 22b without also passing through the barrier layer 36. Alternatively, as shown in FIG. 7A, the sutures 100 may pass through one or both layers 22a and 22b of ingrowth material and surround the reinforcing members 50, 52. Preferably, although not necessarily, the sutures do not pass through the barrier layer 36. The sutures may also encompass the stitch lines 30, as shown, or may be passed around the reinforcing members 50, 52 within the respective channels 54, without also including the stitch lines. The needle typically is left on the sutures and the sutures may be clamped with a suitable instrument, such as a hemostat, and draped out of the way.

In another embodiment, rather than using sutures, staples are used. The staples are inserted into a pocket 32 or 60 (through opening 34 or 62) after the prosthesis is in position in the patient and the prosthesis is stapled accordingly. In yet another embodiment, helical tacks may be used, such as those available from Origin, Inc. As with the staples, the helical tacks are inserted into a pocket 32 or 60 (through opening 34 or 62) after the prosthesis is in position in the patient and the prosthesis is anchored accordingly. It should be appreciated that other suitable anchors may be used, as the present invention is not limited to the use of sutures, staples, tacks or any other particular anchoring mechanism or technique.

A sufficient number of sutures, staples, tacks or other anchors are used to secure the prosthesis. Depending on the size and/or location of the defect, four to twelve or more anchors may be employed, with some of the anchors being disposed on the prosthesis near the edge of the defect and other anchors being disposed on the prosthesis near the peripheral edge 34.

Figure 6:
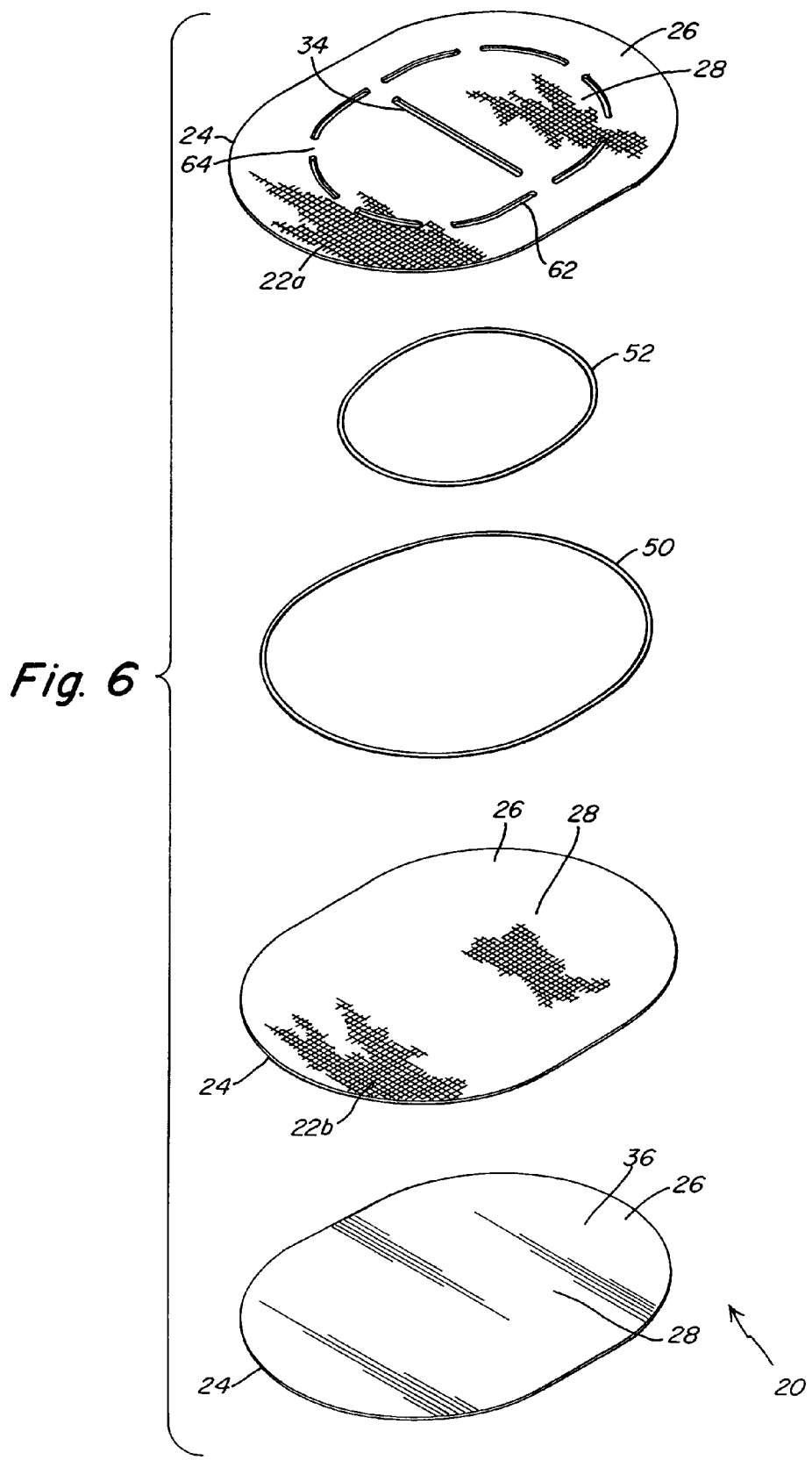
FIG. 6 is an exploded perspective view of the prosthesis of FIG. 1.

In one embodiment, the second pocket 60 includes a plurality of openings 62, spaced circumferentially around area 26 or about member 52, as shown in FIGS. 1 and 6. Preferably, openings 62 are formed though the first layer 22a such that a portion 64 of the first layer connects adjacent spaced openings 62. These portions 64 advantageously limit the amount of billowing of the first layer 22a from the second layer 22b. For example, portions 64 may act as bridges to the inner area 28, the edge of which is secured to layer 22b by stitch line 30b. In one embodiment, to reinforce the edges of the openings 62, and to prevent tearing of layer 22a, a stitch or other reinforcement 66 is formed in portions 64. The reinforcements 66 may have any suitable shape including the arc-shape as shown and may extend through the first and second layers 22a and 22b or through just the first layer 22a.

Although the embodiment described above includes inner and outer pockets, the present invention is not limited in this respect.

In the embodiment shown, the prosthesis 20 is relatively flat and sufficiently pliable to allow a surgeon to manipulate the prosthesis to insert the prosthesis and conform the prosthesis to the anatomical site of interest, allow the prosthesis to be sutured, stapled or otherwise anchored. The prosthesis 20 may be configured to have any suitable shape or size that is conducive to facilitating the correction of a particular defect. In the embodiments illustrated in the figures, the prosthesis 20 has a generally flat, oval shape. Examples of other shapes include, but are not limited to, circular, square, rectangular and irregular shapes.

One example of a procedure to implant the prosthesis 20 will now be described. The defect is identified and the margins are everted. A surgical instrument, such as a bovie, is used to score into either the preperitoneal or retro-muscular space. The surgeon's finger is then inserted and, sweeping circumferentially, a space is created for the prosthesis to lie. The prosthesis may then be rolled and inserted into the space created. As discussed above, the pockets on the prosthesis may be used to aid in insertion. Again sweeping circumferentially with a finger either over or within the pocket, the prosthesis, with the aid of the reinforcing members, if employed, opens up and lies in its preformed shape.

Once the prosthesis is in place, the sutures 100 are passed through the tissue or muscle above the layer 22a from which tissue ingrowth is desired. The sutures 100 are then tied and trimmed. To reduce the amount of distortion on the prosthesis, the sutures 100 should not be under any significant amount of tension. To facilitate manipulating the sutures, the surgeon may enter the pockets 60 through an opening 62 with the appropriate instruments and perform the attachment through the pockets 60. When staples are employed, for example, the surgeon inserts a stapler into a pocket 32 or 60 and staples the first layer 22a to the tissue or muscle from which ingrowth is desired adjacent the edges of the defect and optimally, at the peripheral edge of the prosthesis. The wound is then closed in a suitable fashion. The prosthesis also may be used in open procedures, or in less invasive procedures, such as minimally invasive surgeries and laparoscopic surgeries.

In an exemplary embodiment, layers 22a and 22b each are formed of an approximately 0.027 inch thick sheet of BARD MESH knitted from polypropylene monofilament with a diameter of approximately 0.006 inches. Barrier 36 is formed from an approximately 0.006 to 0.008 inch thick sheet of ePTFE. Barrier 36 is attached to layers 22a and 22b using approximately 3 mm to 4 mm long stitches formed of a 0.008 inch to 0.012 inch diameter PTFE monofilament. The prosthesis 20 typically has a generally oval shape that may have any desired size. For example, the prosthesis, as measured generally along the major and minor axes of the oval, may be approximately sized as follows: 5 inches by 7 inches; 7 inches by 9 inches; 8 inches by 10 inches; or 10 inches by 13 inches. The prosthesis may also be sized to cover an area greater than 50 square cm. In one embodiment, the prosthesis covers an area of approximately 68 square cm; in another embodiment, approximately 119 square cm; in yet another embodiment, approximately 152 square cm; and in still another embodiment, (e.g., for an obese patient) approximately 246 square cm. It should be understood, however, that the materials and dimensions described are merely exemplary and that any suitable sizes and shapes may be employed for the prosthesis.

In one embodiment, the prosthesis is sized such that the prosthesis overlaps the edges of the defect by at least 3 cm and, in some embodiments, by at least 4 cm and in still other embodiments, by at least 5 cm. Also, although the prosthesis has been described above as correcting a single defect, it is contemplated that a suitable sized and shaped prosthesis may be used to correct more than one defect.

It should be understood that the foregoing description of the invention is intended merely to be illustrative thereof and that other embodiments, modifications, and equivalents of the invention are within the scope of the invention recited in the claims appended hereto. Further, the prosthesis described above includes various features that may be employed singularly or in any suitable combination.

What is claimed:

1. An implantable prosthesis for a tissue or muscle defect, the implantable prosthesis comprising:
    a first layer of material that permits tissue or muscle ingrowth;
    a second layer of material that permits tissue or muscle ingrowth, the second layer being attached to the first layer;
    at least one pocket formed between the first and second layers, the at least one pocket including an access opening through the first layer for gaining access to an interior of the at least one pocket;
    a layer of barrier material that is resistant to tissue or muscle ingrowth and the formation of adhesions with tissue or muscle, the layer of barrier material being attached to at least the second layer, the second layer being located between the first layer and the layer of barrier material; and
    a peripheral edge defining a boundary of the prosthesis, wherein the access opening is disposed inward of the peripheral edge.

2. The prosthesis according to claim 1, wherein the at least one pocket is defined by attachment of the first and second layers.

3. The prosthesis according to claim 1, wherein substantial areas of the second layer are free from attachment to the layer of barrier material.

4. The prosthesis according to claim 1, wherein the second layer is constructed and arranged to support stress induced by patient movement.

5. The prosthesis according to claim 1, wherein the prosthesis is constructed and arranged to be provisionally attached to tissue or muscle.

6. The prosthesis according to claim 1, wherein the first and second layers are connected by first stitches that do not extend through the layer of barrier material.

7. The prosthesis according to claim 6, wherein the first and second layers are connected to the layer of barrier material by second stitches.

8. The prosthesis according to claim 7, wherein at least the second stitches are formed from a tissue or muscle adhesion resistant material.

9. The prosthesis according to claim 1, wherein each of the first and second layers includes a plurality of interstices that are constructed and arranged to allow tissue or muscle to grow into the first and second layers.

10. The prosthesis according to claim 1, wherein the peripheral edge is constructed and arranged to resist the formation of tissue or muscle adhesions thereto.

11. The prosthesis according to claim 1, wherein each of the first and second layers comprises polypropylene mesh.

12. The prosthesis according to claim 1, wherein the at least one pocket is sized to receive at least one finger.

13. An implantable prosthesis for a tissue or muscle defect, the implantable prosthesis comprising:
    a first sheet of material that permits tissue or muscle ingrowth;
    a second sheet of material that permits tissue or muscle ingrowth, the second sheet being attached to the first sheet;
    at least one pocket formed between the first and second sheets, the at least one pocket including an access opening through the first layer for gaining access to an interior of the at least one pocket;
    a sheet of absorbable adhesion resistant barrier material that is resistant to tissue or muscle ingrowth and the formation of adhesions with tissue or muscle, the sheet of barrier material being attached to at least the second sheet, the second sheet being located between the first sheet and the sheet of barrier material; and
    a peripheral edge defining a boundary of the prosthesis, wherein the access opening is disposed inward of the peripheral edge.

14. The prosthesis according to claim 13, wherein substantial areas of the second sheet are free from attachment to the sheet of barrier material.

15. The prosthesis according to claim 13, wherein the first and second sheets are connected by first stitches that do not extend through the sheet of barrier material.

16. The prosthesis according to claim 15, wherein the first and second sheets are connected to the sheet of barrier material by second stitches.

17. The prosthesis according to claim 16, wherein at least the second stitches are formed from a tissue or muscle adhesion resistant material.

18. The prosthesis according to claim 13, wherein each of the first and second sheets includes a plurality of interstices that are constructed and arranged to allow tissue or muscle to grow into the first and second sheets.

19. The prosthesis according to claim 13, wherein the peripheral edge is constructed and arranged to resist the formation of tissue or muscle adhesions thereto.

20. The prosthesis according to claim 13, wherein the sheet of barrier material covers an entire surface of the second sheet.

21. The prosthesis according to claim 13, wherein the sheet of barrier material includes ePTFE.

22. The prosthesis according to claim 21, wherein the ePTFE has fibril lengths of less than 5 microns.

23. The prosthesis according to claim 22, wherein the ePTFE has fibril lengths of less than 1 micron.

24. The prosthesis according to claim 23, wherein the ePTFE has fibril lengths of less than 0.5 microns.

25. The prosthesis according to claim 13, wherein each of the first and second sheets comprises polypropylene mesh.

26. An implantable prosthesis for a tissue or muscle defect, the implantable prosthesis comprising:
    a first layer of material that permits tissue or muscle ingrowth;
    a layer of barrier material that is resistant to tissue or muscle ingrowth and the formation of adhesions with tissue or muscle;
    a second layer of material that permits tissue or muscle ingrowth, the second layer being located between the first layer and the layer of barrier material, the second layer being attached to the first layer;
    at least one pocket formed between the first and second layers that is adapted to receive a surgeon's finger to facilitate positioning of the prosthesis;
    an access opening through the first layer to provide access by the surgeon's finger to an interior of the at least one pocket; and
    a peripheral edge defining a boundary of the prosthesis, wherein the access opening is disposed inward of the peripheral edge.

27. The prosthesis according to claim 26, wherein substantial areas of the second layer are free from attachment to the layer of barrier material.

28. The prosthesis according to claim 26, wherein the first and second layers are connected by first stitches that do not extend through the layer of barrier material.

29. The prosthesis according to claim 28, wherein the first and second layers are connected to the layer of barrier material by second stitches.

30. The prosthesis according to claim 29, wherein at least the second stitches are formed from a tissue or muscle adhesion resistant material.

31. The prosthesis according to claim 26, wherein each of the first and second layers includes a plurality of interstices that are constructed and arranged to allow tissue or muscle to grow into the first and second layers.

32. The prosthesis according to claim 26, further comprising a peripheral edge that is constructed and arranged to resist the formation of tissue or muscle adhesions thereto.

33. The prosthesis according to claim 26, wherein the layer of barrier material covers an entire surface of the second layer.

34. The prosthesis according to claim 26, wherein the layer of barrier material includes ePTFE.

35. The prosthesis according to claim 34, wherein the ePTFE has fibril lengths of less than 5 microns.

36. The prosthesis according to claim 35, wherein the ePTFE has fibril lengths of less than 1 micron.

37. The prosthesis according to claim 36, wherein the ePTFE has fibril lengths of less than 0.5 microns.

38. The prosthesis according to claim 26, wherein each of the first and second layers comprises polypropylene mesh.

39. An implantable prosthesis for a tissue or muscle defect, the implantable prosthesis comprising:
   a first layer of material that permits tissue or muscle ingrowth;
   a second layer of material that permits tissue or muscle ingrowth;
   at least one pocket formed between the first and second layers, the at least one pocket sized to receive at least one finger of a surgeon to facilitate positioning of the prosthesis, the at least one pocket including an access opening through the first layer; and
   a layer of barrier material that is resistant to tissue and muscle ingrowth and the formation of adhesions with tissue or muscle, the layer of barrier material being attached to at least the second layer, the second layer being located between the first layer and the layer of barrier material.

40. The prosthesis according to claim 39, wherein the at least one pocket is defined by attachment of the first and second layers.

41. The prosthesis according to claim 39, wherein the at least one pocket includes an access opening for gaining access to an interior of the at least one pocket.

42. The prosthesis according to claim 41, further comprising a peripheral edge defining a boundary of the prosthesis, wherein the access opening is disposed inward of the peripheral edge.

43. The prosthesis according to claim 39, wherein substantial areas of the second layer are free from attachment to the layer of barrier material.

44. The prosthesis according to claim 39, wherein the second layer is constructed and arranged to support stress induced by patient movement.

45. The prosthesis according to claim 39, wherein the first and second layers are connected by first stitches that do not extend through the layer of barrier material.

46. The prosthesis according to claim 45, wherein the first and second layers are connected to the layer of barrier material by second stitches.

47. The prosthesis according to claim 46, wherein at least the second stitches are formed from a tissue or muscle adhesion resistant material.

48. The prosthesis according to claim 39, wherein each of the first and second layers includes a plurality of interstices that are constructed and arranged to allow tissue or muscle to grow into the first and second layers.

49. The prosthesis according to claim 39, further comprising a peripheral edge that is constructed and arranged to resist the formation of tissue or muscle adhesions thereto.

50. The prosthesis according to claim 39, wherein each of the first and second layers comprises polypropylene mesh.

51. An implantable prosthesis for repairing a tissue or muscle defect, the prosthesis comprising:
   a tissue ingrowth layer that permits tissue or muscle ingrowth, the tissue ingrowth layer including a first mesh layer, a second mesh layer attached to the first mesh layer, a pocket located between the first mesh layer and the second mesh layer that is adapted to receive a surgeon's finger and/or a surgical instrument to facilitate positioning and/or attachment of the prosthesis, and an access opening through the first mesh layer to provide access by the surgeon's finger and/or the surgical instrument to an interior of the pocket; and
   an absorbable adhesion resistant barrier layer that is resistant to tissue or muscle ingrowth covering an outer surface of the second mesh layer, the second mesh layer being located between the first mesh layer and the barrier layer.

52. The prosthesis according to claim 51, wherein the pocket has an outer perimeter, the first and second mesh layers being connected together with stitches extending about the outer perimeter of the pocket.

53. The prosthesis according to claim 51, wherein the ingrowth layer includes an outer area that is reinforced to increase the rigidity of the prosthesis.

54. The prosthesis according to claim 53, wherein the outer area surrounds the pocket.

* * * * *